United States Patent
Zheng et al.

(10) Patent No.: US 9,002,078 B2
(45) Date of Patent: Apr. 7, 2015

(54) METHOD AND SYSTEM FOR SHAPE-CONSTRAINED AORTIC VALVE LANDMARK DETECTION

(75) Inventors: Yefeng Zheng, Dayton, NJ (US); Matthias John, Nürnberg (DE); Jan Boese, Eckental (DE); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 1247 days.

(21) Appl. No.: 12/877,168

(22) Filed: Sep. 8, 2010

(65) Prior Publication Data

US 2011/0096969 A1 Apr. 28, 2011

Related U.S. Application Data

(60) Provisional application No. 61/253,882, filed on Oct. 22, 2009.

(51) Int. Cl.
 *G06K 9/00* (2006.01)
 *G06K 9/62* (2006.01)
(52) U.S. Cl.
 CPC .......... *G06K 9/00214* (2013.01); *G06K 9/6209* (2013.01)

(58) Field of Classification Search
 None
 See application file for complete search history.

(56) References Cited

U.S. PATENT DOCUMENTS

| | | | |
|---|---|---|---|
| 4,538,227 A * | 8/1985 | Toraichi et al. | 378/62 |
| 7,539,284 B2 * | 5/2009 | Besson | 378/62 |
| 7,678,052 B2 | 3/2010 | Torp et al. | |
| 8,009,887 B2 * | 8/2011 | Ionasec et al. | 382/128 |
| 8,073,215 B2 * | 12/2011 | Lu et al. | 382/128 |
| 2004/0153128 A1 | 8/2004 | Suresh et al. | |
| 2004/0249281 A1 | 12/2004 | Olstad | |
| 2008/0085050 A1 * | 4/2008 | Barbu et al. | 382/154 |
| 2008/0101676 A1 | 5/2008 | Zheng et al. | |
| 2009/0010519 A1 | 1/2009 | Wakai et al. | |
| 2009/0123050 A1 | 5/2009 | Ionasee et al. | |
| 2009/0177089 A1 * | 7/2009 | Govari et al. | 600/453 |

OTHER PUBLICATIONS

NPL—Yefeng Zheng et al., Fast Automatic Heart Chamber Segmentation from 3D CT Data Using Marginal Space Learning and Steerable Features, 2007 IEEE, 8 pages.*

* cited by examiner

Primary Examiner — Wesley Tucker

(57) ABSTRACT

A system and method for performing shape-constrained aortic valve landmark detection using 3D medical images is provided. A rigid global shape defining initial positions of a plurality of aortic valve landmarks is detected within a 3D image. Each of the plurality of aortic valve landmarks is detected based on the initial positions.

33 Claims, 6 Drawing Sheets

METHOD AND SYSTEM FOR SHAPE-CONSTRAINED AORTIC VALVE LANDMARK DETECTION

This application claims the benefit of U.S. Provisional Application No. 61/253,882, filed Oct. 22, 2009, the disclosure of which is incorporated herein by reference.

BACKGROUND OF THE INVENTION

The present invention relates to medical imaging of the heart, and more particularly, to automatic detection of aortic valve landmarks in medical images of the heart.

Aortic valve disease is the most common valvular disease in developed countries, affecting up to 1.8% of the global population. A damaged aortic valve may be remedied by implantation of an artificial aortic valve. During transcatheter valve implantation surgery, in which implantation of an artificial aortic valve occurs, 2D fluoroscopic images are captured in real time by a C-arm system to provide guidance to physicians performing the implantation. The aortic root structure is distinguishable from its background for only a short period of time after a contrast agent is applied. However, contrast agents are typically toxic and it is preferable that contrast agent usage be minimal.

Additionally, an image of the aortic root must be properly aligned within an image plane to provide a physician with maximum visibility to ensure proper implantation of an aortic valve. The centerline of an aortic root should be perpendicular to the normal of the imaging plane. The aortic root needs to rotate around this centerline properly in order to ensure that two coronary ostia appear well separated on fluoroscopic images because the coronary ostias can be used to provide guidance to physicians to ensure proper implantation of an aortic valve. Currently, physicians need to apply and reapply contrast agents at least a few times in order to achieve a satisfactory C-arm angulation because pertinent details of the valve structure, such as the aortic root and coronary ostia are only visible for a short time period after application of a contrast agent. Specifically, after an initial angulation orientation, physicians capture fluoroscopic images and apply contrast agents to check if the orientation is satisfactory. If not, the C-arm system is rotated to a new position, thus necessitating reapplication of contrast agents.

Aside from angulation information, physicians may also require information regarding specific artificial valves used during surgery. For example, certain valves, e.g., Edwards Sapien valves, are preferably implanted slightly below the coronary ostia to avoid blocking blood flow to the coronary arteries. Similar to a human aortic valve, some artificial valves have three distinct pockets for valve leaflets. These pockets require proper alignment during implantation. Aortic valve landmarks, such as hinge points and commissure points may be used to provide guidance to physicians during implantation of an aortic valve.

Accordingly, a method for automatically detecting aortic valve landmarks in medical images is desirable.

BRIEF SUMMARY OF THE INVENTION

The present invention provides a method and system for automatic aortic valve landmark detection. Embodiments of the present invention automatically determine aortic valve landmarks in a robust and efficient fashion. Embodiments of the invention achieve robust detection of aortic valve landmarks by defining landmarks, assigning labels to each detected landmark, and refining the landmark detections based on initial landmark estimates.

In one embodiment of the present invention, a rigid global shape defining initial positions of a plurality of aortic valve landmarks is detected within a 3D image. Each of the plurality of aortic valve landmarks is detected based on the initial positions defined by the rigid global shape. The rigid global shape may be detected with a trained global shape detector using marginal space learning (MSL). Detecting each of the plurality of landmarks may be performed by determining a search region of each aortic valve landmark based on the initial position of each aortic valve landmark; detecting a new position of each aortic valve landmark within the respective search region using a trained landmark detector; and projecting the new positions of the aortic valve landmarks into a shape subspace of the global shape using an active shape model.

These and other advantages of the invention will be apparent to those of ordinary skill in the art by reference to the following detailed description and the accompanying drawings.

DETAILED DESCRIPTION

Figure 1:
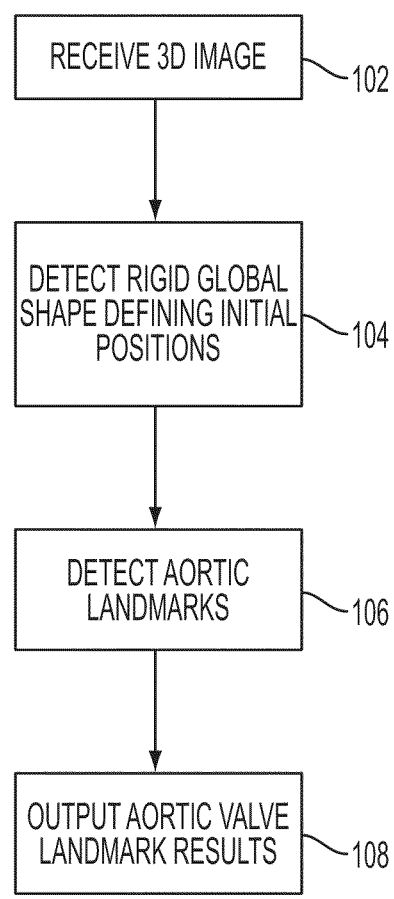
FIG. 1 illustrates a method for determining aortic valve landmarks in a 3D medical image according to an embodiment of the present invention.

The present invention is directed to a method and system for shape-constrained aortic valve landmark detection in 3D medical images, including, but not limited to, DynaCT images, cardiac CT images, and cardiac magnetic resonance imaging (MRI) images. Embodiments of the present invention are described herein to give a visual understanding of aortic valve landmark detection. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within and by a computer system using data stored within the computer system.

DynaCT has recently emerged as an imaging modality offering several advantages over traditional computerized tomography (CT) imaging. DynaCT volumes are generated by rotating an x-ray detector of a C-arm image acquisition system without the need for additional scanners. Accordingly, 3D DynaCT volumes can be captured using the same C-arm image acquisition system. Thus, a 3D patient-specific aorta detected in a 3D DynaCT volume may be overlaid to a 2D x-ray image, which may be performed accurately and efficiently.

However, detection of aortic valve landmarks in a DynaCT volume may present challenges stemming from poor image quality due to reconstruction artifacts and variations in the usage of contrast agents. For example, certain volumes may have high contrast while others have low contrast due to differing amounts of contrast agent applied. Imaging artifacts may cause the coronary ostia to be barely visible or not visible in certain cases. Additionally, aortic hinge points may be difficult to identify due to contrast agent leakage from the aorta to the left ventricle.

Further problems may include high false positive detection rates. To identify a landmark, a specific region around the landmark can be analyzed. However, other regions may have a similar image pattern, especially when the region around the landmark to be analyzed is small. Landmarks may also be inherently ambiguous. For example, the left ostium may be indistinguishable from the right ostium when only a small block cropped around each coronary ostium is used as a reference for landmark detection.

Embodiments of the present invention utilize a shape-constrained approach for detecting aortic valve landmarks in a 3D medical image, such as a DynaCT volume. According to various embodiments of the present invention, the detected aortic valve landmarks may be used for various purposes, including, but not limited to: 1) providing an optimal angulation for a C-arm x-ray system; 2) providing 3D orientation information for implanting artificial valves that are not rotation symmetric; 3) providing an overlay of the detected coronary ostia onto 2D fluoroscopic images to guide physicians in order to prevent blockage of the coronary ostia after valve implantation; and 4) providing 3D measurements of the aortic root for surgery planning.

FIG. 1 illustrates a method for detecting aortic valve landmarks in a 3D medical image according to an embodiment of the present invention. The method of FIG. 1 transforms medical image data representing a cardiac region of a patient to detect and visualize various aortic valve landmarks of the patient.

At step 102, a 3D medical image of an aortic root of a patient is received. According to an embodiment of the present invention, the 3D image can be a DynaCT volume acquired by a C-arm system. However, the present invention is not limited to DynaCT volumes. For example, the 3D image may be a CT or MRI image. The 3D image may be received from an image acquisition device, such as a C-arm image acquisition system, or may be a previously stored volume loaded from a computer readable medium, memory, or storage system of a computer.

At step 104, a global rigid shape is detected, defining initial positions of a plurality of aortic valve landmarks in a 3D medical image. For example, the global rigid shape may define eight aortic valve landmarks: three aortic hinge points ($H_1$, $H_2$, $H_3$), three aortic commissure points ($C_1$, $C_2$, $C_3$), and two coronary ostia ($O_l$ and $O_r$, indicating the left and right ostium, respectively). In order to detect a global rigid shape, a global shape detector can be trained based on annotated training data. The global rigid shape is a shape that encompasses all of the aortic valve landmarks and is detected using the global shape detector, which is trained, using marginal space learning (MSL), based on the annotated training data.

Although it is possible to detect each of the aortic valve landmarks separately, in an advantageous implementation, the hinge points, commissure points, and coronary ostia can be detected in the 3D image using a hierarchical approach which first detects global object (e.g., bounding box) representing all eight anatomical landmarks (3 hinge points, 3 commissures, and 2 coronary ostia) and then refines each individual anatomic landmark using specific trained landmark detectors. The position, orientation, and scale of the global object is detected by classifiers trained based on annotated training data using marginal space learning (MSL). In order to efficiently localize an object using MSL, parameter estimation is performed in a series of marginal spaces with increasing dimensionality. Accordingly, the idea of MSL is not to learn a classifier directly in the full similarity transformation space, but to incrementally learn classifiers in the series of marginal spaces. As the dimensionality increases, the valid space region becomes more restricted by previous marginal space classifiers. In particular, detection of the global object in the 3D image is split into three stages: position estimation, position-orientation estimation, and position-orientation-scale estimation. A separate classifier is trained based on annotated training data for each of these steps. This object localization results in an estimated transformation (position, orientation, and scale) of the object, and a mean shape of the object is aligned with the 3D volume using the estimated transformation. Boundary delineation of the estimated object shape can then be performed by non-rigid deformation estimation (e.g., using an active shape model (ASM)). The specific landmark detectors for the hinge points, commissure points, and coronary ostia can be trained position detectors that search for the specific landmarks in a region constrained by the detected global object. MSL is described in further detail in United States Patent Application No. 2008/0101676 entitled "System and Method for Segmenting Chambers of a Heart in a Three Dimensional Image", which is incorporated herein by reference.

A mean shape m for a set of training global shapes is determined, each mean shape m representing an optimal global shape. Given a group of global shapes $M_1, M_2, \ldots, M_N$, corresponding to various training images, a mean shape m may be determined to represent the entire population of the training data in order to minimize residual errors after alignment. The calculation performed to determine mean shape m can be expressed by Equation (1):

$$m = \operatorname{argmin} \sum_{i=1}^{N} \|T_i(m) - M_i\|^2$$

$T_i$ represents the corresponding transformation from the mean shape m to each individual shape $M_i$. This procedure is called a generalized Procrustes analysis. T represents translation (t=[X,Y,Z]'), rotation (R), and anisotropic scaling ($S_x$, $S_y$, $S_z$). The representation of a 3D point P can be expressed by Equation (2):

$$T(P) = R \begin{bmatrix} S_x & 0 & 0 \\ 0 & S_y & 0 \\ 0 & 0 & S_z \end{bmatrix} P + t$$

Using the Procrustes analysis as specified in Equation (1), an optimal mean shape may be obtained from a training set. Mean shape m needs to be uniquely defined in order to prepare mean shape m for extraction to be used in a training set. The optimal mean shape m is not unique because it can be freely translated, rotated, and scaled. The unnecessary flexibility of mean shape m can be removed by defining a unique orientation for the global shape. Given a mean shape m, the following procedures are implemented to normalize the translation, rotation, and scale of mean shape m. For example, $H_c=(H_1+H_2+H_3)/3$ represents the mass center of three aortic hinge points and $C_c=(C_1+C_2+C_3)/3$ represents the mass center of three aortic commissure points. A z axis is defined as a unit vector pointing from hinge center $H_c$ to the commissure center $C_c$. An initial x axis is defined as a unit vector pointing from the right coronary ostium $O_r$ to the left coronary ostium $O_l$. The x axis is rotated inside the plan spanned by the x and z axes to make the x axis perpendicular to the z axis. The y axis, by consequence, becomes a cross product of the z and x axes.

After defining orientation of a shape, an aligned bounding box is calculated for the mean shape representing aortic valve landmarks. The origin of the object-centered coordinate system is set to the center of the bounding box. The bounding box is scaled anisotropically, resulting in a cube of 1 mm length×1 mm width×1 mm height. The mean shape m is thereafter bounded in a cube and is considered uniquely defined. As a result, an initial position estimate for each individual landmark may be calculated. A mean shape is extracted from the entire training set. A transformation of each training shape toward the mean shape is also extracted in the training set.

Figure 2A:
FIG. 2a illustrates an exemplary image showing aortic valve landmarks of training data before alignment.

FIG. 2a illustrates an exemplary image of aortic valve landmarks before alignment. For this particular figure, the aortic valve landmark data points were gathered from 149 datasets, and represent the mean shape.

The trained global shape detector is used to detect the rigid global shape in the received 3D medical image. As described above, the mean shape m and the ground truth of the transformation T is determined for each shape in the training set. MSL is used to train a global shape detector that can detect the transformation T in an unseen volume.

Figure 2B:
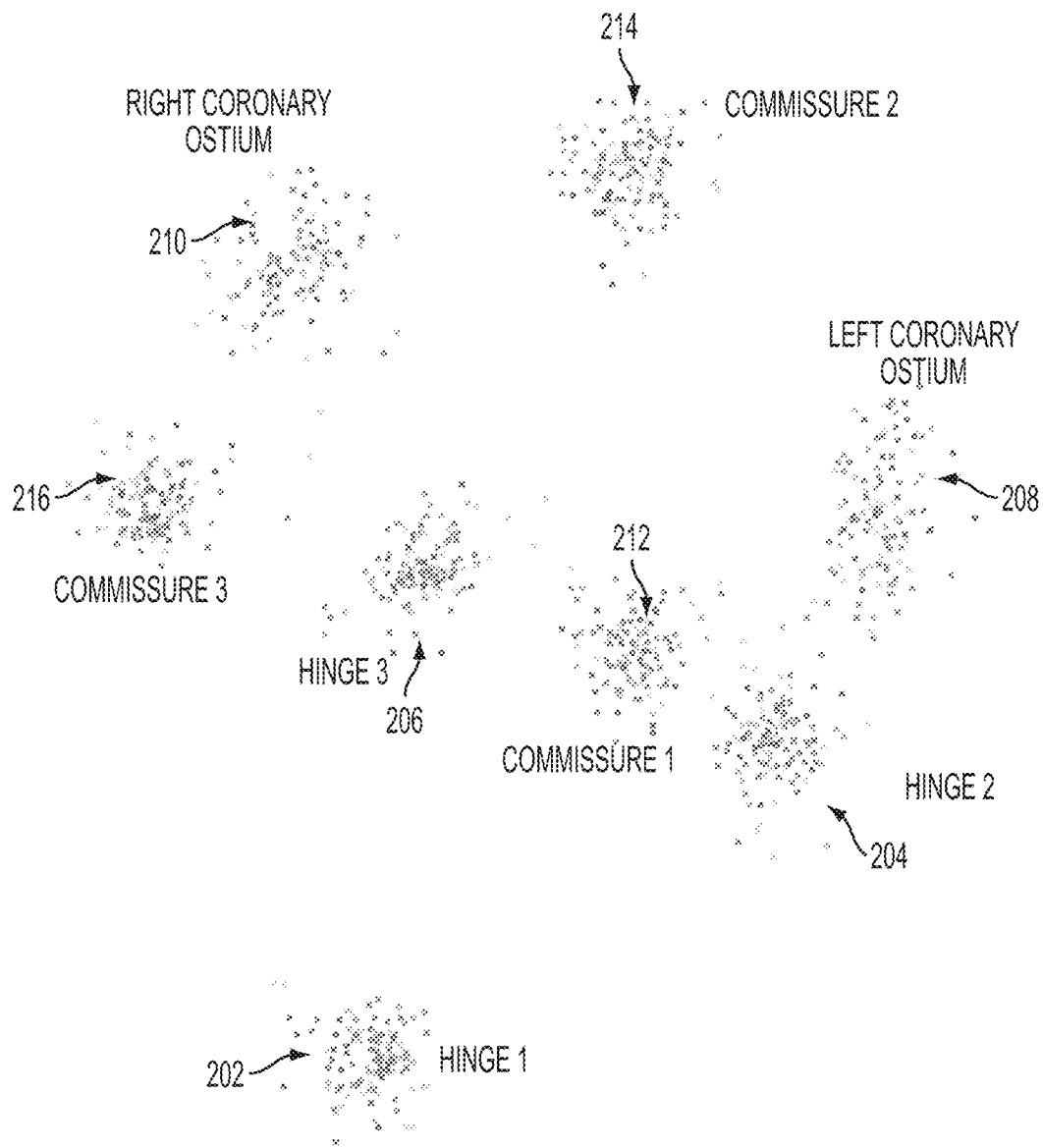
FIG. 2b illustrates an exemplary image showing the aortic valve landmarks of FIG. 2a after alignment.

FIG. 2b illustrates an exemplary image showing the aortic valve landmarks of FIG. 2a after alignment is performed, as described above. After alignment and transformation of the dataset shown in FIG. 2a, the resulting datasets corresponding to each aortic valve landmark are shown in FIG. 2b. For example, 202, 204, and 206 represent hinge points, 208 and 210 represent the left coronary ostium and right coronary ostium, respectively, and 212, 214, and 216 represent commissure points.

Returning to FIG. 1, at step 106, each of the plurality of aortic valve landmarks is detected based on the initial position defined by the rigid global shape. Determination of the position of each landmark may be performed by a position detector. The position detector may be trained using annotated training data representing each landmark. For example, each landmark position detected may be trained using a probabilistic boosting tree (PBT) and steerable features. An iterative process enforces a nonrigid global constraint using statistical shape models by adjusting the landmarks inside a small region based around the initial estimate. A method for detecting the individual aortic valve landmarks based on the global rigid shape is described in detail below.

At step 108, the detected aortic valve landmarks are output. For example, the aortic valve landmarks may be output to a display for physician review. For example, the output may be used to provide the best angulation in a c-arm system or present a physician with 3D orientation or measurement information useful for implanting artificial valves that are not rotation symmetric or useful for helping a physician plan for a surgery. Additionally, the aortic valve landmarks in the 3D medical image may be overlaid onto 2D fluoroscopic images to provide guidance to physicians.

Figure 3:
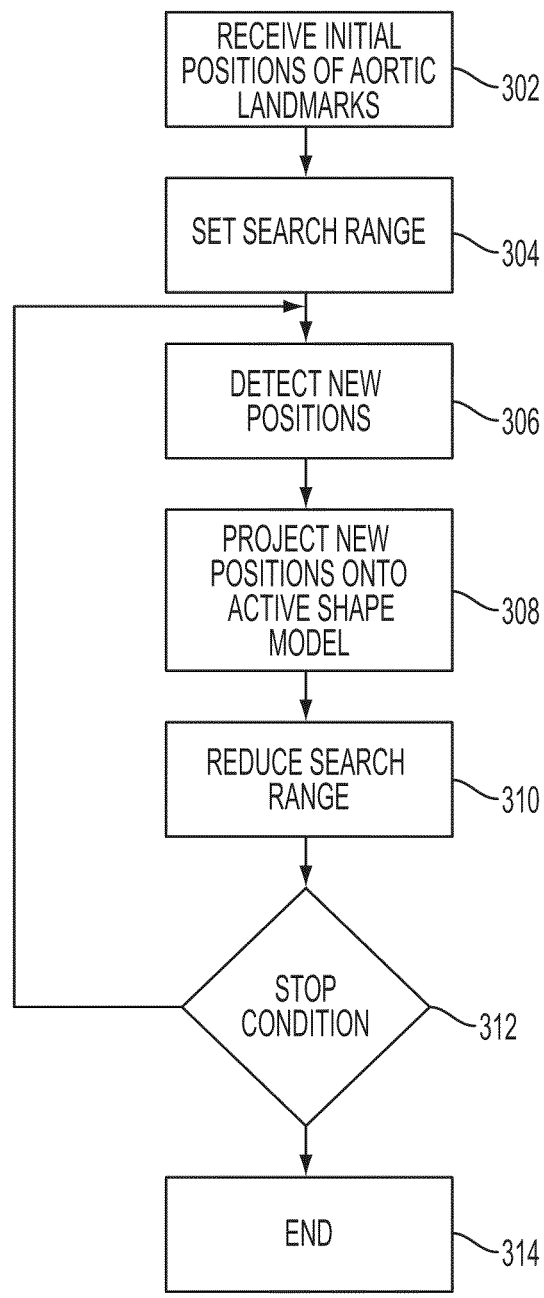
FIG. 3 illustrates a method for detecting individual landmarks based on a global shape model according to an embodiment of the present invention.

FIG. 3 illustrates a method for detecting individual landmarks based on the global rigid shape. This method may be used to implement step 106 of FIG. 1 in order to detect each of the plurality of landmarks defined by the global rigid shape. The iterative process may be performed through the steps described herein. At step 302, the initial positions of a plurality of aortic valve landmarks are received by a local position detector. The initial positions represent an initial estimate of where each aortic valve landmark resides in a 3D image.

At step 304, a search region is set around each initial position. For example, the search region may be represented by r, where r=20 mm, representing the radius of the search region or the length of the sides of a cube which is the search region.

At step 306, a new position of each aortic valve landmark is calculated based on a point within each search region having a highest score value determined by the respective aortic valve landmark positions detected by the local position detector. A separate position detector is trained for each aortic valve landmark. The new position of an aortic valve landmark is detected using the position detector constrained to the search region surrounding the initial position of the aortic valve landmark.

At step 308, the new positions are projected into a shape subspace of the global shape using an active shape model. The active shape model adjusts the new positions of the aortic valve landmarks to enforce a shape constraint in the aortic valve landmark positions. Given a new shape, M, of the aortic valve landmarks, a transformation (translation t, rotation R, and anisotropic scaling S) from M towards the mean shape m is estimated. After the transformation, the aligned shape is represented by N. The statistical shape model is represented as a linear subspace $(m, P_1, P_2, \ldots, P_K)$. Here m is the mean shape, and $P_i$ represents an orthogonal axis of the linear subspace. Shape N is then projected onto the subspace in order to obtain a constrained shape n. This is represented by Equation (3):

$$n = m + \sum_{i=1}^{K} (P_i \cdot N) P_i$$

$P_i.N$ is the dot product of vectors $P_i$ and N, and is therefore a scalar value. The constrained shape n is transferred back into a world coordinate system using the previously estimated translation t, rotation R, and scaling S.

At step 310, the size of the search region is reduced. For example, the size of the search region can be reduced to half of its previous value.

At step 312, it is determined whether a stop condition is reached. According to a possible implementation, the stop condition can be reached when the positions of the aortic valve landmarks converge in the image. According to another possible implementation, the stop condition can be reached when a predetermined number of iterations are performed. When the stop condition is not reached at step 312, the method returns to step 306 and repeats steps 306, 308, 310, and 312 to further adjust the positions of the aortic valve landmarks in the 3D image. When the stop condition is reached at step 312, the method proceeds to step 314. At step 314, the method ends.

Figure 4:
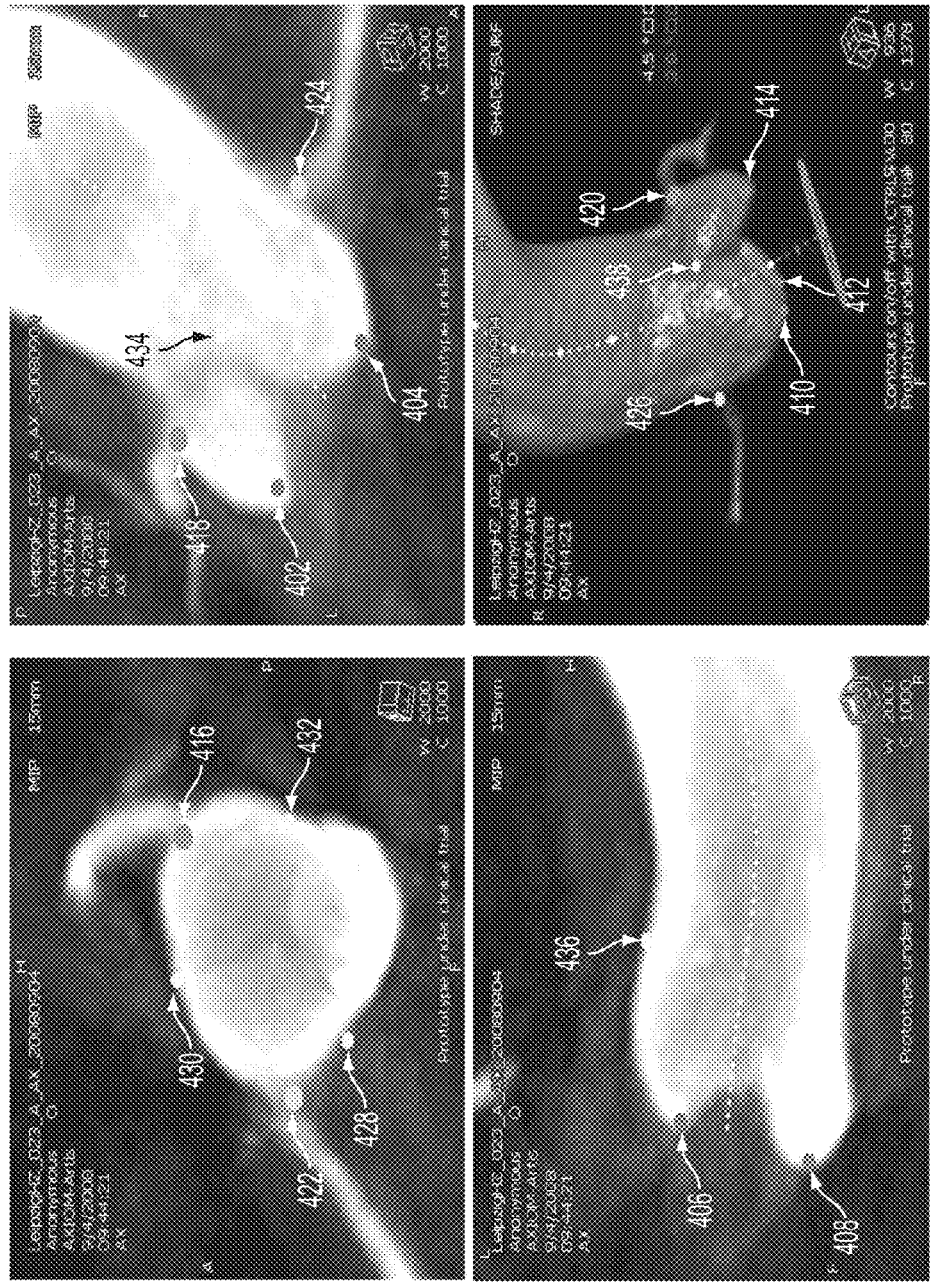
FIG. 4 illustrates aortic valve landmark detection results in various 3D volume datasets according to the embodiments of the present invention.

FIG. 4 illustrates aortic valve landmark detection results in various 3D volume datasets. As illustrated in FIG. 4, points 402, 404, 406, 408, 410, 412, and 414 represent detected hinge points. Points 416, 418, and 420 represent detected left coronary ostium. Points 422, 424, and 426 represent detected right coronary ostium. Points 428, 430, 432, 434, and 436 represent detected commissure points.

Experiments were conducted on 115 patients resulting in 149 DynaCT volumes. The size of each slice in a volume is 256×256 or 512×512 pixels. Each volume contains approximately 200-300 slices. The volume resolution is isotropic, but varies from volume to volume within a range of 0.70-0.84 mm. A four-fold cross validation was performed to evaluate the embodiments described herein. The 149 datasets corresponding to the 149 volumes were split into four sets, each set having approximately the same number of volumes. Three of the four sets for used for training, and the fourth for testing, and each of the sets rotated until all sets were tested once. Error measurements for the tests were also recorded, using the Euclidean distance from the detected landmark to a ground truth value as a measure of accuracy.

TABLE 1

Aortic valve landmark detection errors using a four-fold cross-validation on 149 volumes. The mean, standard deviation (STD), and median of the errors are reported.

| | Aortic Commissures | | | Aortic Hinges | | | Coronary Ostia | | |
|---|---|---|---|---|---|---|---|---|---|
| | Mean | STD | Median | Mean | STD | Median | Mean | STD | Median |
| After Global Pose Estimation | 5.43 | 2.26 | 5.20 | 5.40 | 2.51 | 4.83 | 5.81 | 2.45 | 5.18 |
| Independent Local Refinement | 4.35 | 2.45 | 3.51 | 3.10 | 2.40 | 2.37 | 3.10 | 2.58 | 2.01 |
| Nonrigid Shape Constrained Refinement | 3.46 | 1.78 | 3.11 | 2.41 | 1.50 | 1.90 | 2.74 | 2.43 | 1.77 |

Note:
The errors are measured in millimeters (mm).

Table 1 shows the error measurements during detection of the aortic valve landmarks. The mean errors after global pose estimation range from 5.40 to 5.81 mm for different landmarks. When independent local refinement was applied for each landmark, a reduction in error was achieved. Further error reduction was attained by implementing nonrigid shape constrained refinement. For example, the mean error for the aortic hinges was reduced from 5.40 mm to 2.41 mm.

Figure 5:
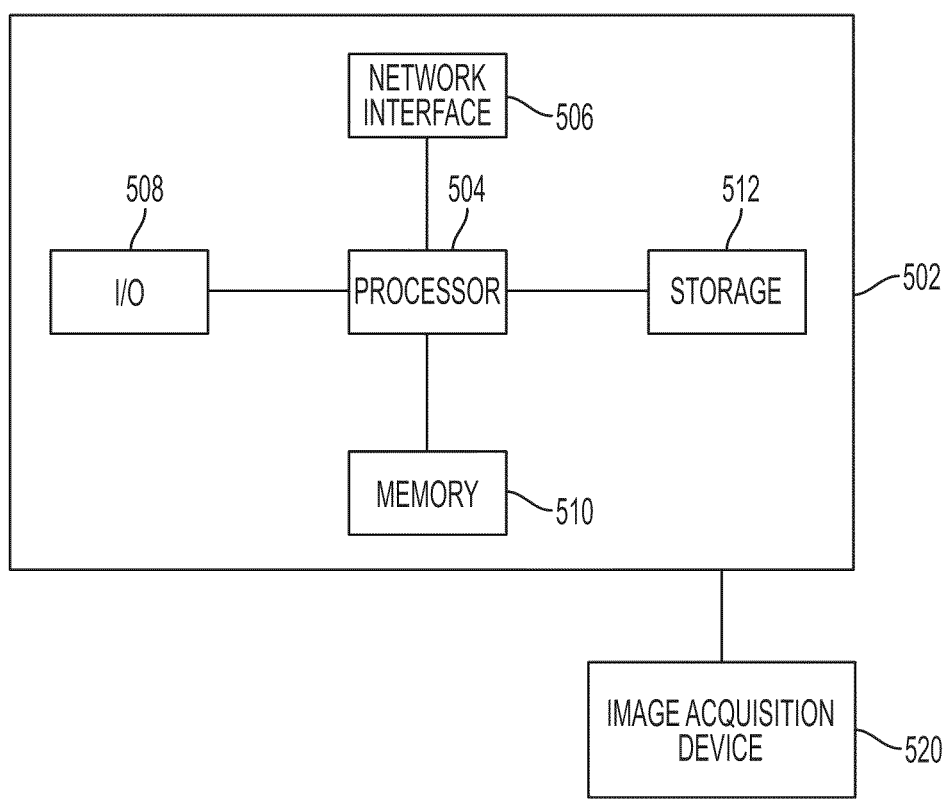
FIG. 5 is a high-level block diagram of a computer capable of implementing the embodiments of the present invention.

The above-described methods for aortic valve landmark detection may be implemented on a computer using well-known computer processors, memory units, storage devices, computer software, and other components. A high-level block diagram of such a computer is illustrated in FIG. 5. Computer 502 contains a processor 504, which controls the overall operation of the computer 502 by executing computer program instructions, which define such operation. The computer program instructions may be stored in a storage device 512, or other computer readable medium, (e.g., magnetic disk) and loaded into memory 510 when execution of the computer program instructions is desired. Thus, all method steps described above, including the method steps illustrated in FIGS. 1 and 2, may be defined by the computer program instructions stored in the memory 510 and/or storage 512 and controlled by the processor 504 executing the computer program instructions. An image acquisition device 520, such as an X-ray imaging device, can be connected to the computer 502 to input fluoroscopic image sequences to the computer 502. It is possible to implement the image acquisition device 520 and the computer 502 as one device. It is also possible that the image acquisition device 520 and the computer 502 communicate wirelessly through a network. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.) One skilled in the art will recognize that an implementation of an actual computer could contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:
1. A method for aortic valve landmark detection, comprising:
   detecting a global rigid shape defining initial positions of a plurality of aortic valve landmarks in a 3D medical image, wherein the global rigid shape is a shape that encompasses all of the plurality of aortic valve landmarks;
   individually detecting each of the plurality of aortic valve landmarks in the 3D medical image within search regions determined based on the initial positions of the plurality of aortic valve landmarks defined by the global rigid shape.

2. The method of claim 1, wherein the 3D medical image is a 3D C-arm computed tomography (CT) image.

3. The method of claim 1, wherein detecting a global rigid shape comprises:
   detecting the global rigid shape with a trained global shape detector using marginal space learning (MSL).

4. The method of claim 1, wherein detecting a global rigid shape comprises:
   detecting a transformation of a mean global shape in the 3D medical image using a global shape detector trained based on training data, wherein the mean global shape is determined based on a plurality of global shapes in the training data and each of the plurality of global shapes in the training data encompasses all of the plurality of aortic valve landmarks in a corresponding training image; and registering the mean global shape to the 3D medical image using the detected transformation.

5. The method of claim 1, wherein individually detecting each of the plurality of aortic valve landmarks comprises:
   (a) determining a respective search region for each aortic valve landmark based on the initial position of each aortic valve landmark defined by the global rigid shape; and
   (b) detecting a new position of each aortic valve landmark within the respective search region defined for that aortic valve landmark using a respective trained landmark detector for that aortic valve landmark.

6. The method of claim 5, wherein individually detecting each of the plurality of aortic valve landmarks further comprises:
   (c) projecting the new positions of the plurality of aortic valve landmarks into a shape subspace of the rigid global shape using an active shape model.

7. The method of claim 6, wherein individually detecting each of the plurality of aortic valve landmarks further comprises:
   (d) reducing the search region for each of the plurality of aortic valve landmarks; and
   (e) repeating steps (b), (c), and (d).

8. The method of claim 1, further comprising:
determining an angulation of a C-arm x-ray system based upon the detected aortic valve landmarks.

9. The method of claim 1, further comprising:
overlaying the detected aortic valve landmarks onto a 2D fluoroscopic image.

10. The method of claim 1, further comprising:
displaying the 3D medical image including the detected aortic valve landmarks.

11. The method of claim 1, further comprising:
labeling the detected aortic valve landmarks in the 3D medical image.

12. An apparatus for aortic valve landmark detection, comprising:
means for detecting a global rigid shape defining initial positions of a plurality of aortic valve landmarks in a 3D medical image, wherein the global rigid shape is a shape that encompasses all of the plurality of aortic valve landmarks;
means for individually detecting each of the plurality of aortic valve landmarks in the 3D medical image within search regions determined based on the initial positions of the plurality of aortic valve landmarks defined by the global rigid shape.

13. The apparatus of claim 12, wherein the 3D medical image is a 3D C-arm computed tomography (CT) image.

14. The apparatus of claim 12, wherein the means for detecting a global rigid shape comprises:
means for detecting the global rigid shape with a trained global shape detector using marginal space learning (MSL).

15. The apparatus of claim 12, wherein the means for detecting a global rigid shape comprises:
means for detecting a transformation of a mean global shape in the 3D medical image using a global shape detector trained based on training data, wherein the mean global shape is determined based on a plurality of global shapes in the training data and each of the plurality of global shapes in the training data encompasses all of the plurality of aortic valve landmarks in a corresponding training image; and
means for registering the mean global shape to the 3D medical image using the detected transformation.

16. The apparatus of claim 12, wherein the means for individually detecting each of the plurality of aortic valve landmarks comprises:
means for determining a respective search region for each aortic valve landmark based on the initial position of each aortic valve landmark defined by the global rigid shape; and
means for detecting a new position of each aortic valve landmark within the respective search region defined for that aortic valve landmark using a respective trained landmark detector for that aortic valve landmark.

17. The apparatus of claim 16, wherein the means for individually detecting each of the plurality of aortic valve landmarks further comprises:
means for projecting the new positions of the plurality of aortic valve landmarks into a shape subspace of the rigid global shape using an active shape model.

18. The apparatus of claim 17, wherein the means for individually detecting each of the plurality of aortic valve landmarks further comprises:
means for reducing the search region for each of the plurality of aortic valve landmarks.

19. The apparatus of claim 12, further comprising:
means for determining an angulation of a C-arm x-ray system based upon the detected aortic valve landmarks.

20. The apparatus of claim 12, further comprising:
means for overlaying the detected aortic valve landmarks onto a 2D fluoroscopic image.

21. The apparatus of claim 12, further comprising:
means for displaying the 3D medical image including the detected aortic valve landmarks.

22. The apparatus of claim 12, further comprising:
means for labeling the detected aortic valve landmarks in the 3D medical image.

23. A non-transitory computer readable medium encoded with computer executable instructions for aortic valve landmark detection, the computer executable instructions defining steps comprising:
detecting a global rigid shape defining initial positions of a plurality of aortic valve landmarks in a 3D medical image, wherein the global rigid shape is a shape that encompasses all of the plurality of aortic valve landmarks;
individually detecting each of the plurality of aortic valve landmarks in the 3D medical image within search regions determined based on the initial positions of the plurality of aortic valve landmarks defined by the global rigid shape.

24. The non-transitory computer readable medium of claim 23, wherein the 3D medical image is a 3D C-arm computed tomography (CT) image.

25. The non-transitory computer readable medium of claim 23, wherein detecting a global rigid shape comprises:
detecting the global rigid shape with a trained global shape detector using marginal space learning (MSL).

26. The non-transitory computer readable medium of claim 23, wherein detecting a global rigid shape comprises:
detecting a transformation of a mean global shape in the 3D medical image using a global shape detector trained based on training data, wherein the mean global shape is determined based on a plurality of global shapes in the training data and each of the plurality of global shapes in the training data encompasses all of the plurality of aortic valve landmarks in a corresponding training image; and
registering the mean global shape to the 3D medical image using the detected transformation.

27. The non-transitory computer readable medium of claim 24, wherein individually detecting each of the plurality of aortic valve landmarks comprises:
  (a) determining a respective search region for each aortic valve landmark based on the initial position of each aortic valve landmark defined by the global rigid shape; and
  (b) detecting a new position of each aortic valve landmark within the respective search region defined for that aortic valve landmark using a respective trained landmark detector for that aortic valve landmark.

28. The non-transitory computer readable medium of claim 27, wherein individually detecting each of the plurality of aortic valve landmarks further comprises:
  (c) projecting the new positions of the plurality of aortic valve landmarks into a shape subspace of the rigid global shape using an active shape model.

29. The non-transitory computer readable medium of claim 28, wherein individually detecting each of the plurality of aortic valve landmarks further comprises:
  (d) reducing the search region for each of the plurality of aortic valve landmarks; and
  (e) repeating steps (b), (c), and (d).

30. The non-transitory computer readable medium of claim 23, further comprising:
  determining an angulation of a C-arm x-ray system based upon the detected aortic valve landmarks.

31. The non-transitory computer readable medium of claim 23, further comprising:
  overlaying the detected aortic valve landmarks onto a 2D fluoroscopic image.

32. The non-transitory computer readable medium of claim 23, further comprising:
  displaying the 3D medical image including the detected aortic valve landmarks.

33. The non-transitory computer readable medium of claim 23, further comprising:
  labeling the detected aortic valve landmarks in the 3D medical image.

* * * * *